US011344743B2

(12) United States Patent
Behler et al.

(10) Patent No.: US 11,344,743 B2
(45) Date of Patent: May 31, 2022

(54) LED ON FLEXIBLE PRINTED CIRCUIT WITH THERMAL PROTECTION FOR PHOTOTHERAPY TREATMENT

(71) Applicant: KONINKLIJKE PHILIPS N.V., Eindhoven (NL)

(72) Inventors: Matthew Lukens Behler, Merrimack, NH (US); David Hunt, Nashua, NH (US); Darrin Paul Milner, Littelton, MA (US)

(73) Assignee: Koninklijke Philips N.V., Eindhoven (NL)

( * ) Notice: Subject to any disclaimer, the term of this patent is extended or adjusted under 35 U.S.C. 154(b) by 30 days.

(21) Appl. No.: 16/495,167

(22) PCT Filed: Mar. 20, 2018

(86) PCT No.: PCT/EP2018/056962
§ 371 (c)(1),
(2) Date: Sep. 18, 2019

(87) PCT Pub. No.: WO2018/172324
PCT Pub. Date: Sep. 27, 2018

(65) Prior Publication Data
US 2020/0139152 A1    May 7, 2020

Related U.S. Application Data

(60) Provisional application No. 62/474,188, filed on Mar. 21, 2017.

(51) Int. Cl.
*A61N 5/06* (2006.01)
(52) U.S. Cl.
CPC .... *A61N 5/0621* (2013.01); *A61N 2005/0627* (2013.01); *A61N 2005/0645* (2013.01); *A61N 2005/0652* (2013.01)

(58) Field of Classification Search
CPC .......... A61N 5/0621; A61N 2005/0627; A61N 2005/0645; A61N 2005/0652; A61B 5/44;
(Continued)

(56) References Cited

U.S. PATENT DOCUMENTS 6,290,713 B1 * 9/2001 Russell ................ A61N 5/0616
607/88
6,596,016 B1 * 7/2003 Vreman ............... A61N 5/0621
128/903
(Continued)

FOREIGN PATENT DOCUMENTS

FR        2958171 A1 * 10/2011 ........... A61N 5/0621
JP     2003092144 A      3/2003
(Continued)

OTHER PUBLICATIONS

"Prudenziati, M., Printed resistive sensors for physical quantities, 2012, Materials Science and Applications in Sensors, Electronics, and Photonics, Woodhead Publishing Series in Electronic and Optical Materials, pp. 167-192" (Year: 2012).*
(Continued)

*Primary Examiner* — Jennifer Pitrak McDonald
*Assistant Examiner* — Michael T. Holtzclaw

(57) ABSTRACT

A phototherapy device includes a clothing item. Illuminators are secured to the clothing item and arranged to illuminate at least a portion of a patient wearing the clothing item. The illuminators include light emitting diodes (LEDs) mounted on at least one flexible printed circuit board (PCB). A temperature sensor is secured to the clothing item and positioned to measure a temperature proximate to the patient wearing the clothing item. A control circuit is connected to receive the temperature from the temperature sensor and operative to turn off the illuminators responsive to the temperature exceeding a maximum permitted temperature.

13 Claims, 4 Drawing Sheets

(58) Field of Classification Search
CPC ............... A61B 5/6802; A61B 5/6804; A61B 2018/00791; A61B 2918/00797; A61F 7/0097
See application file for complete search history.

(56) References Cited

U.S. PATENT DOCUMENTS

| | | | | |
|---|---|---|---|---|
| 9,756,700 | B2* | 9/2017 | Trouwborst | H05B 45/58 |
| 10,603,509 | B2* | 3/2020 | Van Abeelen | A61N 5/0621 |
| 2007/0088410 | A1* | 4/2007 | Chung | A61N 5/0621 |
| | | | | 607/91 |
| 2007/0233208 | A1* | 10/2007 | Kurtz | A61N 5/0613 |
| | | | | 607/88 |
| 2009/0018622 | A1* | 1/2009 | Asvadi | A42B 1/244 |
| | | | | 607/91 |
| 2010/0174345 | A1 | 7/2010 | Ashdown | |
| 2010/0179469 | A1* | 7/2010 | Hammond | A61N 5/0624 |
| | | | | 604/20 |
| 2011/0092863 | A1 | 4/2011 | Kim | |
| 2011/0301673 | A1* | 12/2011 | Hoffer | A61N 5/0613 |
| | | | | 607/91 |
| 2012/0253433 | A1* | 10/2012 | Rosen | A61N 5/0621 |
| | | | | 607/91 |
| 2015/0224340 | A1 | 8/2015 | Ajiki | |
| 2016/0016792 | A1 | 1/2016 | Fang | |
| 2019/0209861 | A1* | 7/2019 | Dankers | A61N 5/0621 |

FOREIGN PATENT DOCUMENTS

| | | | | |
|---|---|---|---|---|
| WO | | 2007091188 A2 | 8/2007 | |
| WO | WO-2009139877 A1 * | | 11/2009 | ............... A61F 7/02 |
| WO | | 2016016792 A1 | 2/2016 | |
| WO | WO-2018026680 A1 * | | 2/2018 | ........... A61B 5/6804 |
| WO | WO-2018031570 A1 * | | 2/2018 | ............... A61B 5/01 |

OTHER PUBLICATIONS

International Search Report and Written Opinion, International Application No. PCT/EP2018/056962, dated Jul. 20, 2018.

* cited by examiner

LED ON FLEXIBLE PRINTED CIRCUIT WITH THERMAL PROTECTION FOR PHOTOTHERAPY TREATMENT

This application is the U.S. National Phase application under 35 U.S.C. § 371 of International Application No. PCT/EP2018/056962, filed on 20 Mar. 2018, which claims the benefit of U.S. Provisional Application No. 62/474188, filed 21 Mar. 2017. These applications are hereby incorporated by reference herein.

FIELD

The following relates generally to the phototherapy arts, infant safety monitoring arts, jaundice treatment arts, and related arts.

BACKGROUND

Infant jaundice is a common condition manifesting as yellowish skin discoloration. It is believed to be attributable to excess bilirubin pigmentation due to poor neonatal liver function. As bilirubin can have toxic effects, the excess bilirubin may need to be controlled until the infant's liver function improves. Currently, phototherapy devices exist for the treatment of jaundice. In these devices, applied light breaks down the bilirubin thereby providing therapeutic effect. In some designs, the phototherapy device includes a fiber-optic blanket with a separate light engine whose light is distributed over the surface of the infant by way of optical fibers whose ends are embedded in the blanket.

The following discloses new and improved systems and methods to deliver phototherapy to an infant.

SUMMARY

In one disclosed aspect, a phototherapy device includes a clothing item. Illuminators are secured to the clothing item and arranged to illuminate at least a portion of a patient wearing the clothing item. The illuminators include light emitting diodes (LEDs) mounted on at least one flexible printed circuit board (PCB). A temperature sensor is secured to the clothing item and positioned to measure a temperature proximate to the patient wearing the clothing item. A control circuit is connected to receive the temperature from the temperature sensor and operative to turn off the illuminators responsive to the temperature exceeding a maximum permitted temperature.

In another disclosed aspect, a method of delivering phototherapy includes: with illuminators secured to an infant blanket or garment, illuminating at least a portion of an infant wearing the infant blanket or garment in which the illuminators include light emitting diodes (LEDs) mounted on at least one flexible printed circuit board (PCB); with a temperature sensor secured to the infant blanket or garment, measuring a temperature proximate to the infant wearing the infant blanket or garment; with a control circuit, receiving the temperature from the temperature sensor; and with the control circuit, turning off the illuminators responsive to the temperature exceeding a maximum permitted temperature.

In another disclosed aspect, a phototherapy device includes a clothing item. Illuminators are secured to the clothing item and arranged to illuminate at least a portion of a patient wearing the clothing item. The illuminators include light emitting diodes (LEDs) mounted on at least one flexible printed circuit board (PCB). A temperature sensor is secured to the clothing item and disposed on the PCB. The temperature sensor is positioned to measure a temperature proximate to the patient wearing the clothing item. A control circuit is connected to receive the temperature from the temperature sensor and operative to: turn off the illuminators responsive to the temperature exceeding a maximum permitted temperature; and turn on the illuminators responsive to the temperature being below a threshold temperature that is lower than the maximum permitted temperature.

One advantage resides in providing a phototherapy device that combines light emitting diode (LED) and thermal protection components on a flexible printed circuit to reduce the number of parts required for assembly of a phototherapy device.

Another advantage resides in providing a phototherapy device with a reduced number of electrical interconnects.

Another advantage resides in reducing the number of layers in a phototherapy device by combining the LED and thermal protection onto a single flexible printed circuit layer.

Another advantage resides in reducing manufacturing complexity and cost of a phototherapy device, including parts procurement, stock transactions, lead time and manufacturing assembly time.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the invention.

DETAILED DESCRIPTION

Figure 1:
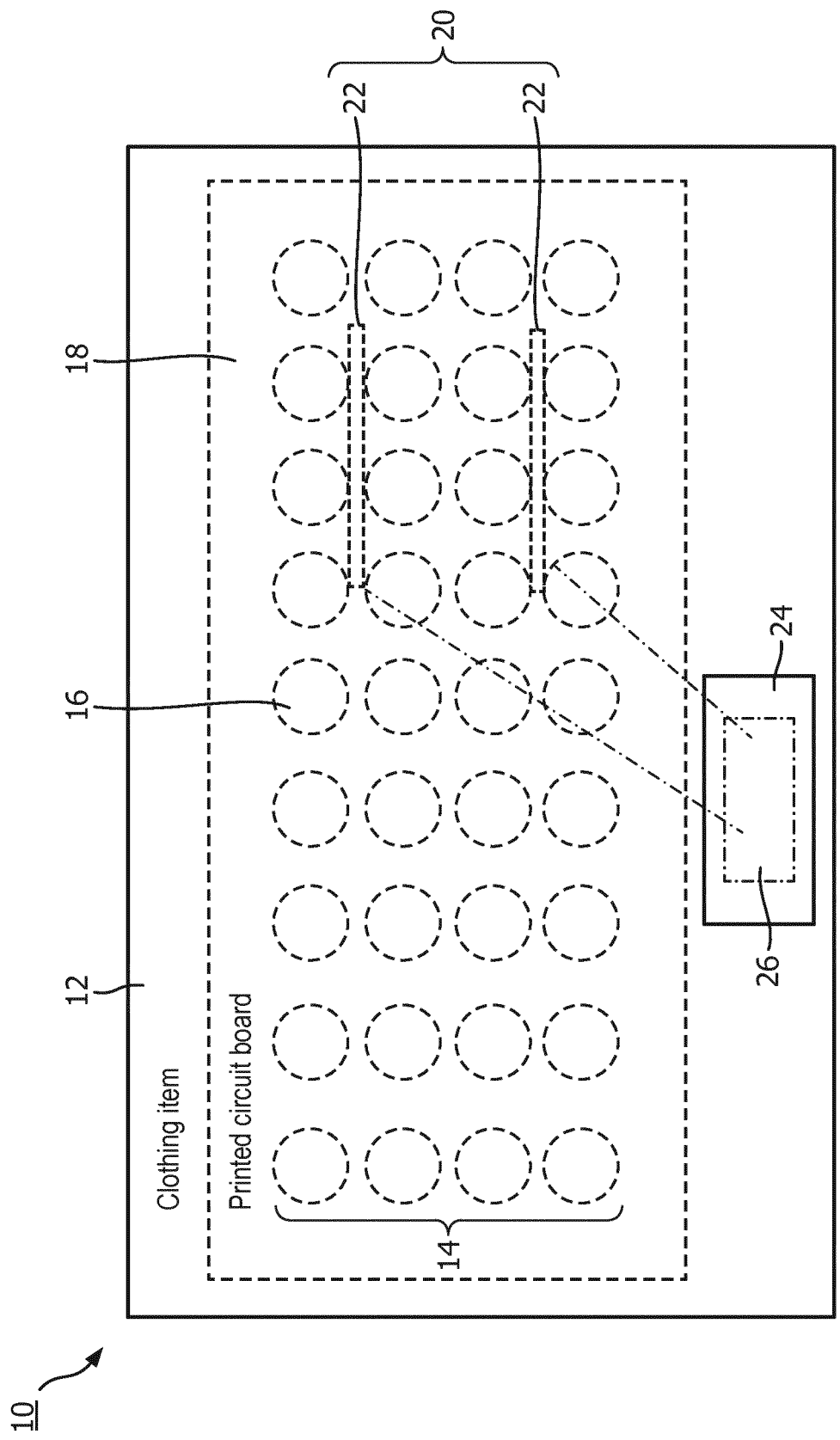
FIG. 1 diagrammatically shows a device for delivering phototherapy to a patient according to one aspect.

The following relates a garment-based phototherapy device for treatment of jaundice, and especially infant jaundice. In some disclosed embodiments, a phototherapy device subassembly combines light emitting diodes (LEDs) on a flexible printed circuit integrated with an item of clothing (e.g. an infant blanket or garment) with an embedded thermal feedback circuit that senses the temperature at the infant's skin. This feedback ensures the user does not overheat as a result of the phototherapy device. The phototherapy device combines LEDs, a thermal protection circuit and a flexible printed circuit to create a LEDs with thermal protection flexible circuit subassembly.

Embodiments of the disclosed phototherapy device can be built using LEDs and thermal sensing components mounted (e.g. soldered) to a flexible printed circuit to make a subassembly component containing an electrical circuit. This subassembly is then integrated with the clothing item and driven with electricity to power the LEDs and thermal sensing circuit. A control circuit monitors the thermal sensing circuit and turn off the phototherapy device if/when a pre-defined phototherapy device temperature is reached.

A possible difficulty with an LED-based phototherapy blanket or garment is excessive heating of the patient's skin by the LEDs. To maintain flexibility, the flexible PCB either has no ground plane, or the ground plane must be made thin, and hence the flexible PCB may not be able to serve as a sufficient heat sink to prevent excessive heating. In typical phototherapy devices, the patient is placed on top of the device, and then the device (with the patient on it) is placed on top of a mattress (or other insulating material), which can limit the ability to provide heat sinking away from the patient. In the infant medical device space, applicable regulations generally require that any surface designed to come into contact with the infant's skin must be maintained at below a safe temperature, e.g. a maximum permissible temperature of 40-43° C. an illustrative example. International regulations and standards (such as IEC 60601-2-50) specify a maximum permissible temperature of 40° C. for surfaces designed to come into contact with the infant's skin, and other surfaces of the device that are accessible for the patient, but which are not designed to come into contact with the patient, must be maintained at below 40° C. for metal surfaces and 43° C. for surfaces on non-metal materials.

The disclosed phototherapy devices leverage a flexible PCB to provide a substrate for a temperature sensor (for example, a negative temperature coefficient thermocouple or thermoresistor, i.e. NTC thermocouple or thermoresistor). A common connector suitably has wires carrying power to the PCB for driving the LEDs and also includes wires to carry the temperature reading back to the main board of the control assembly. Two (or more) NTC devices are contemplated for redundancy, and if either one or both (or, more generally, any) NTC device reads at or above the maximum permissible temperature then the blanket (i.e., all LEDs of the blanket) are immediately turned off until the temperature falls back to a turn-on threshold (which is preferably lower than the maximum permissible temperature so as to form a "dead band" to avoid undesirable power cycling). The temperature sensor is preferably proximate to the infant's skin; however, the flexible PCB is located with the fabric of the blanket or garment disposed between the PCB and the infant's skin. To position the temperature sensor proximate to the infant's skin, it is contemplated to mount the temperature sensor on a finger extending upward through the fabric. The fabric already has aperture openings for passing the LED light, so this merely entails adding the finger to the flexible PCB and aligning it with an additional aperture opening. The finger may, for example, be made of a springy or resilient material that presses the temperature sensor positioned at the distal end of the finger against the skin without presenting a pressure or skin puncture hazard.

With reference to FIG. 1, an illustrative phototherapy device 10 for delivery of phototherapy to a patient is shown. As shown in FIG. 1, the device 10 includes a clothing item 12, such as an infant blanket or garment, that is configured (e.g. sized and shaped) to be worn by a patient (i.e., an infant in the case of an infant phototherapy device). Illuminators 14 are secured to the clothing item 12. For example, the illuminators 14 are distributed across at least a portion of a surface of the clothing item 12. The illuminators 14 are configured to illuminate at least a portion of the patient that is wearing the clothing item 12. This illumination comprises phototherapy delivered to the patient.

In some examples, the illuminators 14 can include light emitting diodes (LEDs) 16 that are mounted on at least one flexible printed circuit board (PCB) 18. Advantageously, the PCB 18 provides a substrate for the LEDs 16 (and other possible components of the device 10) to be mounted on, thereby reducing the number of parts required for assembly of a phototherapy device. The flexible PCB 18 can employ a suitable flex circuit technology, e.g. including a flexible substrate made of polyimide, polyester, or so forth, with conductors formed by screen printing, etching, or so forth. In some embodiments the flexible PCB 18 is constructed as a plurality of parallel strips or other multiple-component configurations (e.g. see FIG. 2). The LEDs 16 are selected to emit light in a therapeutically effective wavelength or wavelength range—for efficient bilirubin breakdown blue light is commonly employed, although other therapeutically suitable spectra are contemplated.

The phototherapy device 10 also includes a temperature sensor 20 configured to measure a temperature proximate to the patient wearing the clothing item 12. For example, the temperature sensor 20 is configured to measure the temperature at an interface between the clothing item 12 and the skin of the infant. In one embodiment, the temperature sensor 20 includes at least two negative temperature coefficient (NTC) devices 22 configured to measure the temperature of the patient. However, the temperature sensor 20 can include any suitable temperature measurement device. Multiple NTC devices 22 are preferably provided for redundancy to measure the temperature proximate the patient, as described in more detail below. In some examples, the temperature sensor 20 is secured to a portion of the clothing item 12 with a wire passing through the fabric of the clothing item. In other examples, the temperature sensor 20 is disposed on the PCB 18.

The device 10 further includes a control circuit 24 that is operatively connected to the illuminators 14 and the temperature sensor 20. The control circuit 24 may, for example, comprise a microprocessor or microcontroller and ancillary electronic components such as a memory chip (e.g. EPROM, EEPROM, flash memory, et cetera), discrete components (e.g. resistors, capacitors), and/or so forth, with (for example) the memory chip storing executable code (e.g. software or firmware) executable by the microprocessor or microcontroller to perform processing functions as described herein. Optionally, the control circuit 24 may additionally or alternatively include analog processing circuitry, e.g. an operational amplifier (op-amp) circuit designed to compare inputs including a temperature sensor reading from the temperature sensor 20 and a reference signal corresponding to the maximum permissible temperature and to generate a control signal based on the comparison. In one example, the control circuit 24 is configured to receive the measured temperature from the temperature sensor 20. In some instances, the measured temperature can be high, which is indicative of overheating of the infant. The control circuit 24 is operatively connected to the illuminators 14 to turn off the illuminators 14 when the temperature exceeds a maximum permitted temperature value, thereby allowing the infant's skin to cool down. In one example, this maximum permitted temperature is 40° C. in accordance with international standards (e.g., IEC 60601-2-50) for surfaces of a medical device that are intended to contact an infant's skin. When the measured temperature falls below a second, minimum threshold (i.e., the patient has cooled down and is no longer overheated), the control circuit 24 is configured to turn the illuminates 14 on to continue the delivery of phototherapy to the infant. The minimum threshold is preferably less than the maximum threshold, and in some non-limiting illustrative examples is preferably slightly higher than approximately 37° C., which is typically the body temperature of the infant.

The control circuit 24, in some examples, is not integral with the clothing item 12, but rather is a separate module. To connect the control circuit 24 to the clothing item 12, the phototherapy device 10 includes a connector 26 secured to a portion of the clothing item 12. As shown in FIG. 1, the control circuit 24 is configured to fit over the connector 26 with a friction fit. Screws (not shown) or another suitable fastener can be used to secure the control circuit 24 to the connector 26. The connector 26 is configured to deliver electrical power to the PCB 18, and thereby deliver power to the LEDs 16 (depicted in FIG. 1 with a first, bolded dashed connector line) in a suitable manner (e.g., batteries, a power cable, and the like). The connector 26 is configured to receive the measured temperature from the temperature sensor 20, and deliver the temperature to the control circuit 24 for processing (depicted as a second, bolded dashed connector line). Advantageously, this single connector 26 reduces the number of components needed for the device 10, while improving the reliability of the device.

Figure 2:
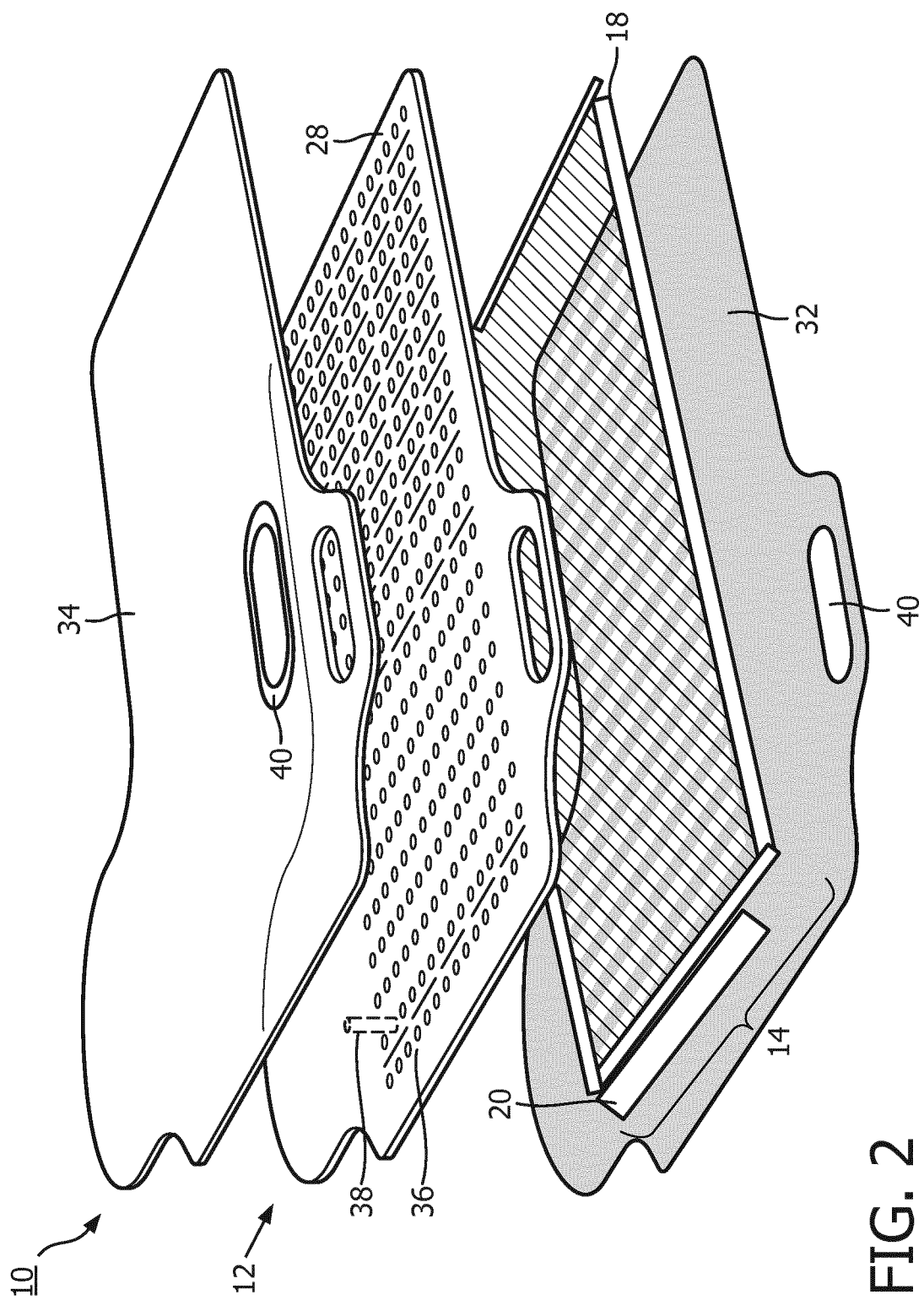
FIG. 2 diagrammatically shows an assembly view of the device of FIG. 1.

Referring now to FIG. 2 (and with continuing reference to FIG. 1), the clothing item 12 is shown in more detail. As shown in FIG. 2, the clothing item 12 is multi-layered. For example, the clothing item 12 includes a fabric layer 28, a back layer 32, and an insulating layer 34 disposed between the fabric layer and the infant wearing the clothing item. The PCB 18, which supports the LEDs 16, is disposed between the back panel 32 and the fabric layer 28. The illustrative PCB 18 of FIG. 2 comprises a series of parallel strips each carrying a "row" of LEDs 16, but other physical layouts are contemplated including a single PCB spanning the entire area of illumination. When assembled, the illuminators 14 are secured to the fabric layer 28. The fabric layer 28 is a three-dimensional (3-D) layer of material, typically a woven fabric, that includes openings (i.e. apertures) 36 to pass light from the LEDs 16 to the infant's skin. As shown in FIG. 2, the temperature sensor 20 is positioned proximate the infant's skin, while also being attached to the PCB 18, and thus the temperature sensor is also secured to the fabric layer 28. In some examples, the temperature sensor 20 is mounted on a finger 38 extending from the PCB 18 through the fabric layer 28. The fabric layer 28 can include an additional aperture (not shown) configured to accommodate the finger 38. The back panel 32 includes an aperture 40 that, when the clothing item 12 is assembled, is configured to accommodate the control circuit 24. The insulating layer 34 can be optically transparent, or at least translucent, to pass light from the LEDs 16.

Figure 3:
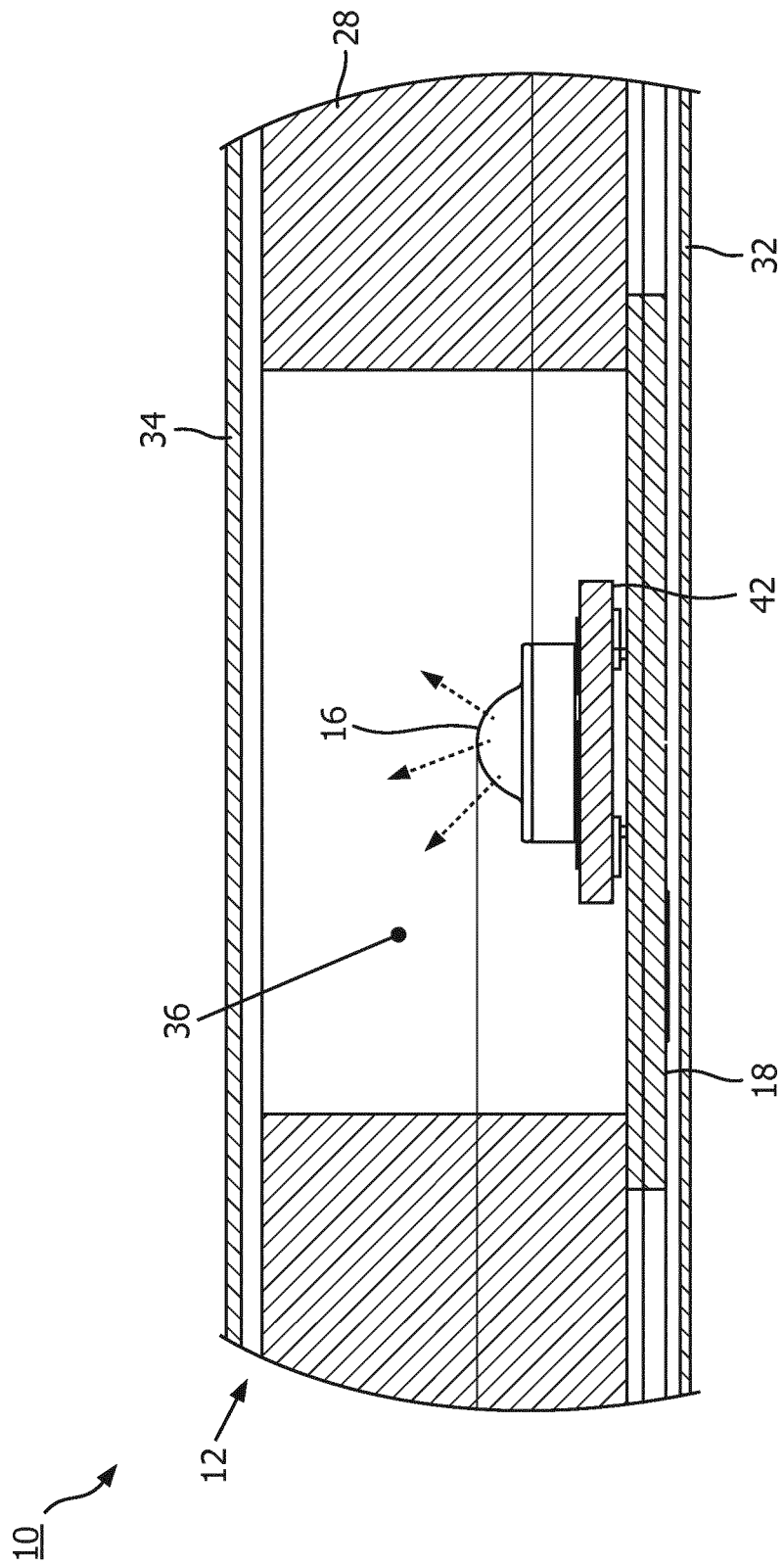
FIG. 3 diagrammatically an internal portion of the device of FIG. 1.

FIG. 3 shows a side view of a portion of the clothing item 12 in more detail. As shown in FIG. 3, the fabric layer 28 includes the apertures or openings 36 so that light from the LEDs 16 can pass to the infant (depicted in FIG. 3 as dashed arrows). The fabric layer 28 performs the usual function of fabric in a blanket or garment, e.g. providing cushioning, comfort, warmth via enhanced body heat retention, ensuring an appropriate distance between the patient and the LEDs 16 to provide a correct intensity value and homogeneity of the phototherapy treatment, et cetera. The LEDs 16 are mounted on the PCB 18 which is disposed between the fabric layer 28 and the back panel 32. Optionally, the LED 16 can be mounted on a base plate or sub-mount 42, which is secured to, and disposed on, the PCB 18.

Figure 4:
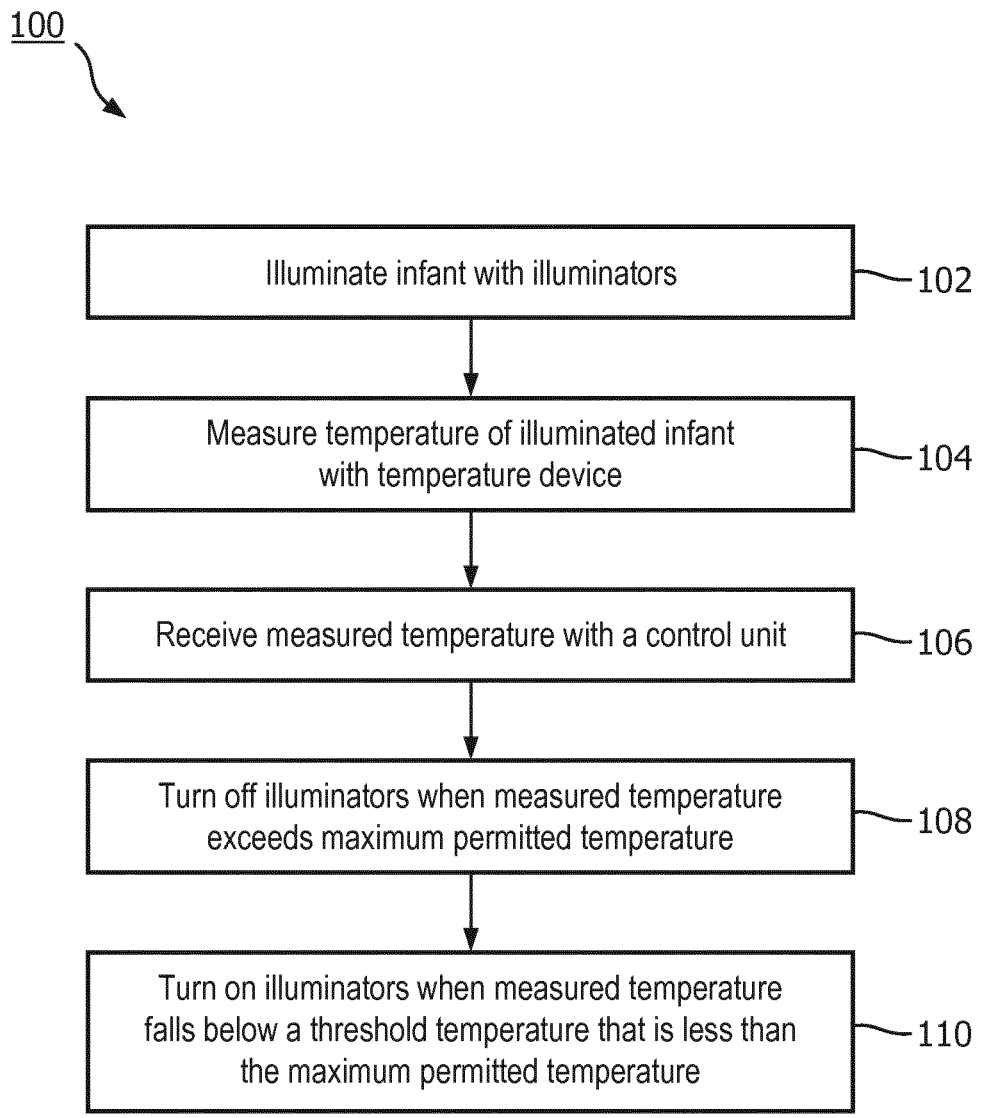
FIG. 4 diagrammatically shows an operational flow chart for operation of the device of FIG. 1.

With reference to FIG. 4, operation of the device 10 is diagrammatically flowcharted as a phototherapy delivery method 100. At 102, at least a portion of an infant wearing an infant blanket or garment 12 is illuminated with illuminators 14 secured to the infant blanket or garment. The illuminators 14 include light emitting diodes (LEDs) 16 mounted on at least one flexible printed circuit board (PCB) 18. In some examples, the illuminators 14 are secured to a fabric layer 28 of the infant blanket or garment 12 with apertures 36 to pass light through the fabric layer. The insulating layer 34 is suitably transparent or translucent to pass the light.

At 104, a temperature proximate to the infant wearing the infant blanket with a temperature sensor 20 secured to the infant blanket 12. In some examples, the temperature sensor 20 is secured on the PCB 18. In other examples, the temperature sensor 20 is mounted on a finger 38 extending from the PCB 18 through the fabric layer 28 of the infant blanket 12. (Note that the front insulating layer 34 is generally very thin, so that the temperature sensor 20 measures close to true skin temperature through the thin insulating layer 34). In some embodiments, the temperature sensor 20 includes at least two negative temperature coefficient devices 22 to measure the temperature of the infant.

At 106, the temperature measured by the temperature sensor 20 is received with a control circuit 24. In some embodiments, the control circuit 24 is not secured to the infant blanket 12. Rather, a connector 26 that the control circuit 24 to the infant blanket 12. The connector 26 is secured to the infant blanket 12. The connector 26 is configured to receive the measured temperature from the temperature sensor 28 and transmit the measured temperature to the control circuit.

At 108, the illuminators 14 are turned off with the control circuit 24 responsive to the measured temperature exceeding a maximum permitted temperature. In some embodiments, the connector 26 is configured to deliver electrical power to the PCB 18, thereby supplying power to the illuminators 14. The control circuit 24 is then configured to shut off the power from the connector 26 to the illuminators 14 when the measured temperature exceeds the maximum permitted temperature. For example, the maximum permitted temperature can be approximately 40° C.

At 110, the illuminators 14 are turned on with the control circuit 24 when the measured temperature is below a threshold temperature that is lower than the maximum permitted temperature. For example, the illuminators 14 are turned off when the maximum permitted temperature (i.e., approximately 40° C.). When the measured temperature falls below a threshold temperature that is less than approximately 40° C. (i.e., approximately 37° C., which is typically the body temperature of the infant), the control circuit 24 is configured to control the connector 26 to again deliver power to the PCB 18, and thereby turn on the illuminators 14 to resume delivering phototherapy to the infant.

The disclosure has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:
1. A phototherapy device, comprising:
 illuminators secured to a clothing item and arranged to illuminate at least a portion of a patient wearing the clothing item, the illuminators including light emitting diodes (LEDs) mounted on at least one flexible printed circuit board (PCB);
 a temperature sensor secured to the clothing item and positioned to measure a temperature proximate to the patient wearing the clothing item; and a control circuit connected to receive the temperature from the temperature sensor and operative to turn off the illuminators responsive to the temperature exceeding a maximum permitted temperature;

wherein the clothing item comprises a fabric layer, the illuminators being secured to the fabric layer, and wherein the temperature sensor is mounted on a finger extending from the flexible PCB through at least the fabric layer, and wherein the finger comprises a resilient material configured such that during use of the device, a distal end of the finger is positioned against skin of the patient wearing the clothing item, and further wherein the fabric layer comprises an aperture configured to accommodate the finger therethrough.

2. The device of claim 1, wherein the temperature sensor is disposed on the PCB.

3. The device of claim 1, wherein the control circuit is further operative to turn on the illuminators responsive to the temperature being below a threshold temperature that is lower than the maximum permitted temperature.

4. The device of claim 3, wherein the temperature sensor includes at least two negative temperature coefficient (NTC) devices configured to measure the temperature of the patient; and the control circuit is operative to turn off the illuminators responsive to the temperature measured by either one or both of the NTC devices exceeding the maximum permitted temperature.

5. The device of claim 1, wherein the control circuit is not secured to the clothing item and the phototherapy device further includes:

a connector for connecting the control circuit with the clothing item and configured to:

deliver electrical power to the at least one flexible PCB of the illuminators; and receive the temperature from the temperature sensor.

6. The device of claim 1, wherein the maximum permitted temperature is 43° C. or lower.

7. The device of claim 1, wherein the clothing item further comprises an insulating layer disposed between the fabric layer and the patient wearing the clothing item.

8. The device of claim 1, wherein wherein the clothing item is a blanket or garment.

9. A method of delivering phototherapy, the method comprising:

with illuminators secured to an infant blanket or garment, illuminating at least a portion of an infant wearing the infant blanket or garment, the illuminators including light emitting diodes (LEDs) mounted on at least one flexible printed circuit board (PCB);

with a temperature sensor secured to the infant blanket or garment, measuring a temperature proximate to the infant wearing the infant blanket or garment;

with a control circuit, receiving the temperature from the temperature sensor; and with the control circuit, turning off the illuminators responsive to the temperature exceeding a maximum permitted temperature;

wherein the clothing item comprises a fabric layer, the illuminators being secured to the fabric layer, and wherein the temperature sensor is mounted on a finger extending from the flexible PCB through at least the fabric layer, and wherein the finger comprises a resilient material configured such that during use of the device, a distal end of the finger is positioned against skin of the patient wearing the clothing item, and further wherein the fabric layer comprises an aperture configured to accommodate the finger therethrough.

10. The method of claim 9, further including:

securing the temperature sensor on the PCB.

11. The method of claim 9, further including:

with the control circuit, turning on the illuminators responsive to the temperature being below a threshold temperature that is lower than the maximum permitted temperature.

12. The method of claim 9, wherein the control circuit is not secured to the infant blanket or garment and the method further includes:

with a connector connecting the control circuit with the infant blanket or garment, delivering electrical power to the at least one flexible PCB of the illuminators; and with the connector, receiving the temperature from the temperature sensor.

13. The method of claim 9, further including an insulating layer of the infant blanket or garment.

* * * * *